US00PP25656P3

(12) United States Plant Patent
Maillard et al.

(10) Patent No.: US PP25,656 P3
(45) Date of Patent: Jun. 30, 2015

(54) PEACH TREE NAMED 'CRISPSUN'

(50) Latin Name: ***Prunus persica* (L.) Batsch**
Varietal Denomination: CRISPSUN

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 166 days.

(21) Appl. No.: 13/815,932

(22) Filed: Mar. 18, 2013

(65) Prior Publication Data

US 2013/0263339 P1 Oct. 3, 2013

(30) Foreign Application Priority Data

Apr. 2, 2012 (QZ) ..... PBR 2012/0742

(51) Int. Cl.
*A01H 5/08* (2006.01)

(52) U.S. Cl.
USPC ..... Plt./197
CPC ..... *A01H 5/0868* (2013.01)

(58) Field of Classification Search
USPC ..... Plt./197
CPC ..... A01H 5/0868; A01H 5/0837; A01H 5/08
See application file for complete search history.

*Primary Examiner* — June Hwu
(74) *Attorney, Agent, or Firm* — Westerman, Hattori, Daniels & Adrian, LLP

(57) ABSTRACT

A new and distinct variety of yellow peach tree denominated 'CRISPSUN' has fruits with high eating quality and very long shelf life without alteration before and after harvesting, with a semi-sweet orange yellow flesh showing a red pigmentation under the skin, inside and around the pit cavity, and an attractive luminous skin with a high percentage of red blush on skin surface.

4 Drawing Sheets

Botanical classification: *Prunus persica* (L.) Batsch.
Variety denomination: 'CRISPSUN'.

This application claims priority of Community plant variety right No. 2012/0742 filed on Apr. 2, 2012 (Apr. 2, 2012) which is hereby incorporated by reference in its entirety.

BACKGROUND OF THE NEW VARIETY

The present invention relates to a new and distinct variety of yellow peach tree, *Prunus persica* (L.) Batsch, which has been given the variety denomination 'CRISPSUN'. This new tree produces fruits with a long shelf life without alteration both on the tree after growth completion and after harvesting, very good eating quality, clingstone orange yellow flesh fruits for fresh market in August in the Pyrénées-Orientales department (an administrative district), France. Contrast is made to 'CRISPDELICE SUN' yellow peach tree (U.S. Plant Pat. No. 19,231), and to its female parent, 'CRISPREGAL' (U.S. Plant Pat. No. 19,178) yellow peach tree, for reliable description. 'CRISPSUN' is a promising candidate for commercial success in that it has very attractive fruits with very long shelf life without alteration both before and after harvesting.

ORIGIN OF THE VARIETY

The 'CRISPSUN' yellow peach tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'CRISPSUN' variety resulted from an open-pollination of the 'CRISPREGAL' (U.S. Plant Pat. No. 19,178) yellow peach tree, which was used as the seed parent. Thus, the pollen parent is unknown.

'CRISPSUN' was provisionally designated, tested and genetically identified by a genetic profile, under number 4S.12W.49PJ and was registered at the Official Catalogue of the Agriculture Ministry of the French Republic on Nov. 27, 2011 under number 4049388 The 'CRISPSUN' variety was obtained by hybridizing and propagated by grafting on a 'INRA GF677' rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales , France. More particularly, the plant was reproduced by grafting.

SUMMARY OF THE VARIETY

The new and distinct variety 'CRISPSUN' yellow peach tree blooms at the end of February or during March near Elne in the Pyrénées-Orientales department, France. More particularly, the blooming begins between March, 1st and March 18th generally together with 'Bigtop' yellow nectarine tree (non patented). The 'CRIPSUN' variety blooms generally 2 or 3 days earlier than 'JULIEPRETTY' yellow peach tree (U.S. Plant Pat. No. 20,611). The blooming period is considered medium. However, it was observed that its early date of blooming seems to be highly dependant on climatic conditions.

The first fruit of 'CRISPSUN' ripens generally at the end of July or early in August, approximately 8 days earlier than 'CRISPDELICE SUN' yellow peach variety (U.S. Plant Pat. No. 19,231). More particularly, it usually ripens between July 16th and August 5th. However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
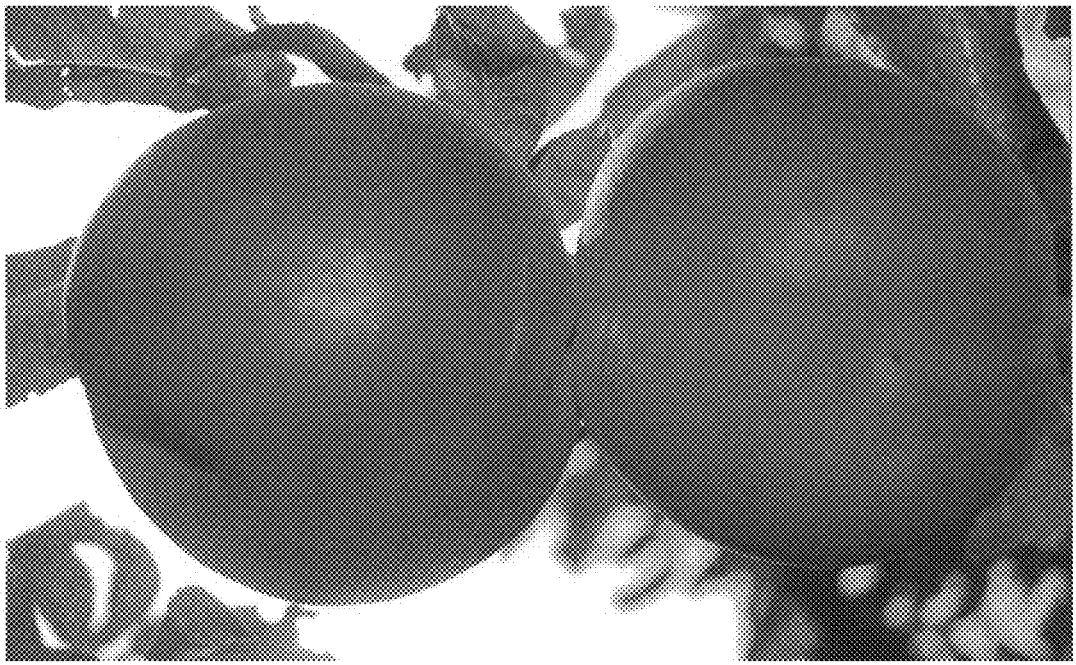
FIG. 1 is a color photograph showing a branch of a tree of the new variety in its third leaf, in orchard, bearing fruits.
Figure 2:
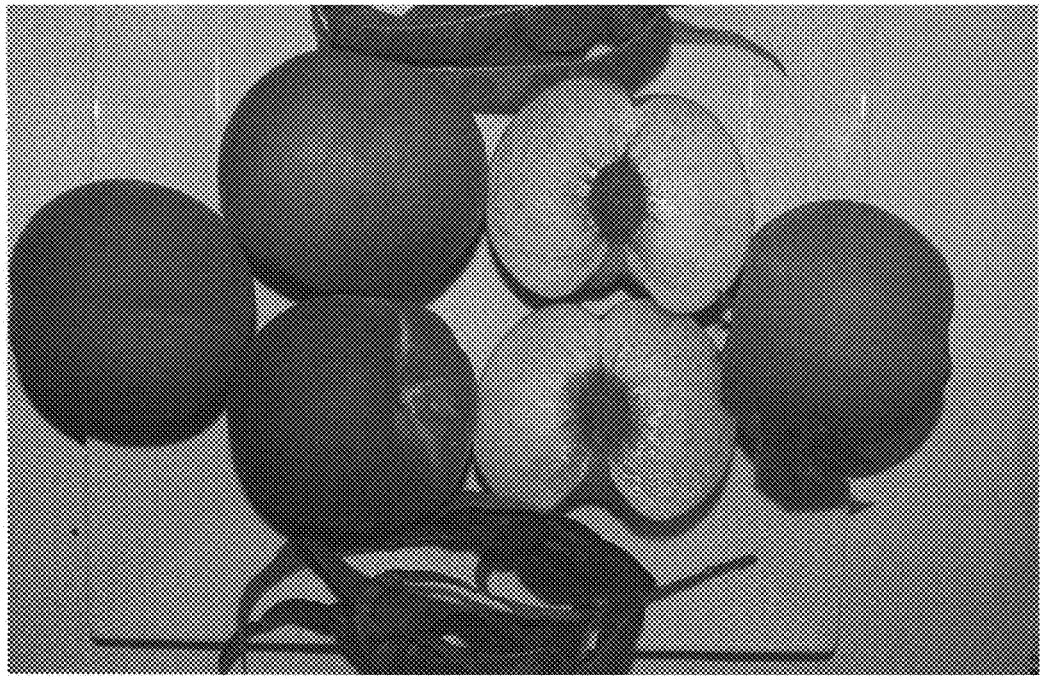
FIG. 2 is a color photograph which shows five typical specimens of the fruit, one having been cut in half with the pit being left in one of the halves for depicting leaves, fruit flesh, pit and pit cavity of the new variety.
Figure 3:
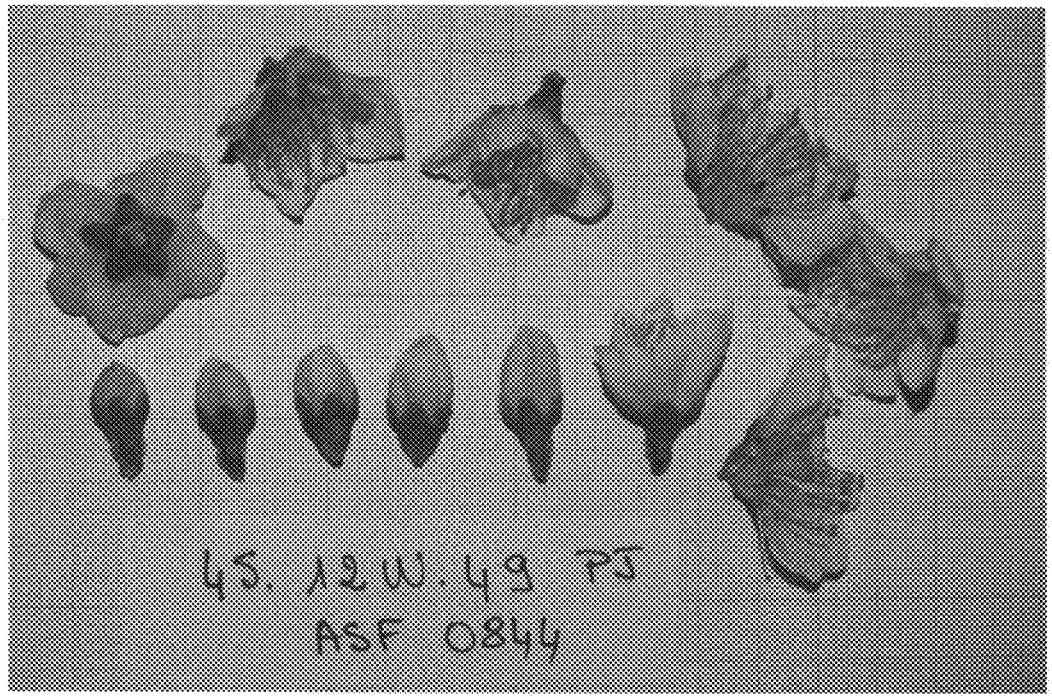
FIG. 3 is a color photograph which depicts the flower buds at different development stages, and the reverse and side view of the flower and the reproductive organs with petals removed, of the new variety.
Figure 4:
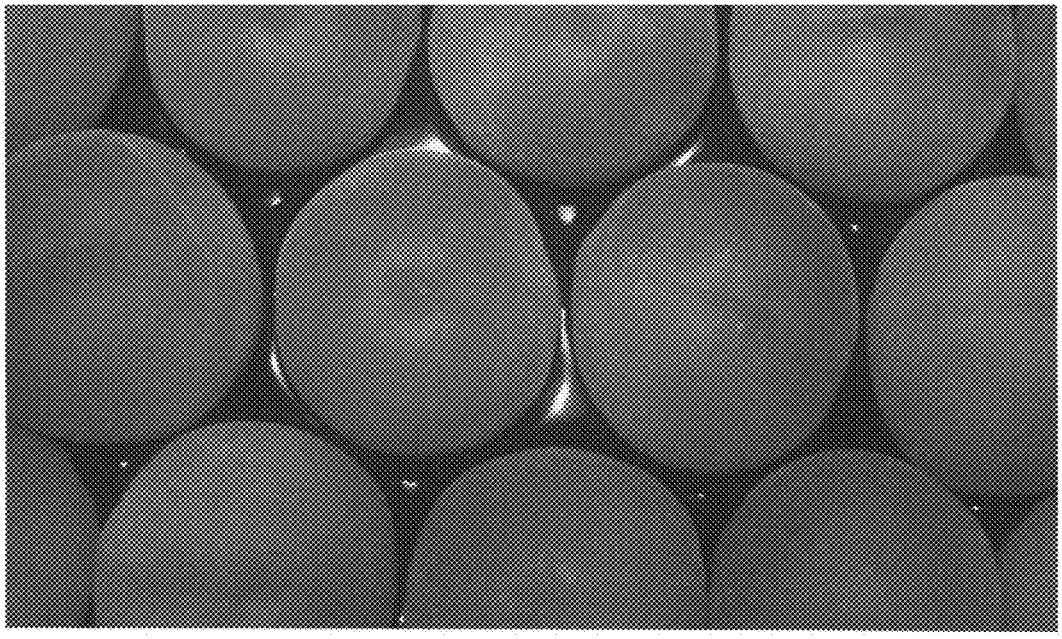
FIG. 4 is a color photograph that shows a close view of typical fruits of the new variety 'CRISPSUN' at ripening time.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruits by 'CRISPSUN' is high, due to fruit very long shelf life without alteration after harvesting.

Trees are medium vigorous and large stature half-standing in a semi-flared to semi-upright out aspect. The anthocyanic coloration of flowering shoot is present excluding brushwood side away from sun. The time of beginning of flowering is considered medium for the variety; flowering begins at the end of February or in March. The type of flower is showy with medium to large petal size. Petals are pale pink. Leaf glands are present and reniform. The fruit flesh is orange yellow and its skin is thick, colored with a luminous red blush on an orange background. The stone is clingstone and his size is medium. Fruit taste is semi-sweet, aromatic and with a high level of sugars.

Compared to 'CRISPDELICE SUN' (U.S. Plant Pat. No. 19,231) yellow peach tree, the 'CRISPSUN' variety approximately ripens 8 days earlier, as set forth above. 'CRISPSUN' fruits color is more intense than 'CRISPDELICE SUN' fruits color. 'CRISPSUN' variety produces a higher quantity of flowers than 'CRISPDELICE SUN' variety.

The new variety male parent is unknown. Indeed, 'CRISPSUN' variety was obtained from an open pollination of the 'CRISPREGAL' (U.S. Plant Pat. No. 19,178) variety.

The new variety female parent, which is the 'CRISPREGAL' (U.S. Plant Pat. No. 19,178) variety, produces yellow peaches approximately 1 week earlier than 'CRISPSUN' variety. However, 'CRISPSUN' fruits are more attractive, because the coloration of their skin is more intense and luminous than skin coloration of 'CRISPREGAL' fruits.

DETAILED DESCRIPTION

Referring more specifically to the pomological details of this new and distinct variety of yellow peach tree, the following was observed on trees in their fourth growing season (third year of production) under the ecological conditions prevailing at the orchards located near the town of Elne, Pyrénées-Orientales department, France. All observations have been done on rootstock cultivars. Used rootstocks were 'INRA GF677' trees. All major color code designations are by reference to The R.H.S. Colour Chart 2001 (Fourth Edition) provided by The Royal Horticultural Society of Great Britain.

Tree:

*Size*.—Generally. — Considered large. The tree size the first year was approximately 250 cm. The tree was pruned during each following dormant season to a height of approximately 250 cm. Current season shoots growth could reach 60 to 80 cm. The tree size from the second year (second and next years) reached a final height of 310 to 330 cm including current season shoots length. The tree size is consistently reduces to 250 cm the next years.

*Spread*.—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor*.—Considered medium vigorous.

*Productivity*.—Very Productive and regular, every year. Fruit set is spaced by thinning to develop the remaining fruit into the desired market sized fruit. The number of the fruit set varies with the prevailing climatic conditions and cultural practices employed during the bloom period, and is therefore not distinctive of the present variety.

*Bearer*.—Very regular. The fruit distribution is considered homogenous on mixed branches and spurs having more than 1 year. Thinning of 1 fruit out of 3 was necessary for the tree valorisation. Thinning was necessary every year during the years of observation.

*Form*.—The 'CRISPSUN' variety has naturally a semi-flared to semi-upright shape.

*Density*.—Considered dense.

*Hardiness*.—The present tree was grown and evaluated in France. The variety appears to be hardy under the central Pyrénées-Orientales department typical climatic conditions. Experimentations on different sites with winter chilling requirement comprised between 350 hours and 1200 hours showed a good behaviour of the tree in all cases. No damages were caused by ascertained temperatures as low as −12 degrees Celsius in winter. The tree was also very resistant to frosty springtime weather.

Trunk:

*Diameter*.—Approximately 13.0 to 14.0 centimetres in diameter when measured at a distance of approximately 30 cm above the soil level.

*Bark texture*.—Considered slightly rough, with lenticels.

*Lenticels*.—Numerous lenticels are present. The number of lenticels reaches 4 or 5 lenticels per $cm^2$. The lenticels range in size from approximately 5.0 to 7.0 millimeters in width, and from 2.0 to 3.0 millimeters in height.

*Lenticel color*.—The outside of lenticels has a silver-grey color (RHS Grey 201 D or RHS Black 202 D), whereas the inside of lenticels is considered brown (RHS Greyed Orange 166 B).

*Bark coloration*.—The bark has a silver-grey color (RHS Grey 201 A), slightly darker than lenticels color.

Branches:

*Size*.—Mature branches and current season shoots are considered medium to large for the variety.

*Diameter*.—Average as compared to other peach varieties. The current season shoots have a diameter from 5.0 to 7.0 millimeters, and mature branches have a diameter from 32.0 to 40.0 millimeters.

*Surface texture*.—Average, wood which is several years old has no furrowed appearance.

*Crotch angles*.—Primary branches are considered variable, but the crotch angles are generally between 80 degrees and 90 degrees from the horizontal axis. This particular characteristic is not considered distinctive of the variety, however.

*Current season shoots*.—Surface texture. — Substantially glabrous.

*Internode length*.—Generally between 12.0 millimeters and 19.0 millimeters.

*Color of mature branches*.—Brown (RHS Brown 200 C to D).

*Current seasons shoots*.—Color. — The color of new shoot tips is considered a pale green (RHS Green 144 A to B) on lower part of new shoot tips, whereas the upper part is darker than the lower part and colored in orange brown (RHS Greyed Red 182 B to C). The upper part color is more or less deep, depending on the level on the new shoot tip.

Leaves:

*Size*.—Considered medium for the species. The ratio leaf length/leaf width is 3.27.

*Leaf length*.—Approximately 117.0 to 153.0 millimeters with leaf petiole. The medium length is 133.0 millimeters.

*Leaf width*.—Approximately 34.0 to 47.0 millimeters. The medium width is 41.0 millimeters.

*Leaf base shape*.—Cuneate.

*Leaf form*.—Lanceolate.

*Leaf tip form*.—Short, pointed and acuminate.

*Leaf color*.—Upper leaf surface. — Dark Green (RHS Green 137 A). Lower surface. — A green (RHS Green 137 B to RHS Green 137 C) slightly lighter than the upper leaf surface color.

*Leaf texture for both surfaces* (*upper and lower*).—Smooth.

*Leaf venation*.—Pinnately veined.

*Mid-vein*.—Color. — Light green, almost white cream (RHS Yellow Green 145 D). The color may evolve with maturity.

*Leaf margins*.—Slightly undulating.

*Form of leaf margins*.—Considered slightly dentate.

*Uniformity*.—Leaves are isolated or grouped by 2 or 3. In this last case, one leaf of normal size is found with one or two smaller leaves (at least 50% smaller).

*Leaf petioles*.—Size. — Considered medium. Length. — About 8.0 to about 10.0 millimeters. Diameter. — About 1.5 millimeters.

*Petioles color*.—Upper petiole surface. — Light green (RHS Yellow Green 144 A). Lower surface. — Light green (RHS Yellow Green 145 B).

*Leaf glands*.—Size. — Considered medium. Their length is about 1.5 millimeters and their width is about 1.0 millimeter. Number. — Generally between 2 to 4 glands per leaf. Type. — Reniform. Color. — On young leaves, leaf glands color is considered a light green (RHS Green 145 B). On older leaves, leaf glands color turns to a dark brown (RHS Grey Brown 199 A to 199 B). Margins. — Smooth and regular.

*Leaf stipules*.—Generally. — No leaf stipules were observed. But as seen in the characteristic relative to the leaves uniformity, it is possible to find leaves by groups of 2 or 3, with a normal-size leaf and smaller ones.

*Leaf bud burst*.—Medium.

Flowers:

*Flower buds*.—Generally. — At pre-floral stage of development, the floral buds show an elongated shape, conic in form with a round tip. Their form is evolving until blooming, with variables dimensions. Just before blooming, floral buds are approximately 12.0 millimeters wide and approximately 18.0 millimeters long. Color. — This characteristic is dependent upon the proximity to bloom. At pre-floral stage of development, the bottom of the flowers buds, formed by the sepals, is of purple-brown color (RHS Greyed Purple 183 A); the corolla, formed by the petals, is generally of pink color (RHS Red Purple 65 B or RHS Red Purple C). Petals color shows an evolution until the end of flowering.

*Hardiness*.—The buds are considered hardy under typical central Pyrénées-Orientales department climatic conditions. No winter injury was noted during the last several years of evaluation in the central Pyrénées-Orientales department, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom*.—The blooming time generally begins at the end of February or early in March. The first bloom was observed on Feb. 26, 2009.

*Blooming time*.—Considered medium season in relative comparison to other commercial peach cultivars grown in the Pyrénées-Orientales department, France. The date of full bloom is observed on March, $2^{nd}$ at the middle of the blooming period. The date of bloom varies slightly with climatic conditions and cultural practices. Thus the beginning of the first full bloom was observed on February $26^{th}$, and the end was on Mar. 7, 2009. The next observed blooming times were from Mar. 18 to Mar. 24, 2010 then from Feb. 27 to Mar. 10, 2011 and then from Mar. 14 to Mar. 23, 2012.

*Duration of bloom*.—Approximately 10 days. This characteristic varies slightly with the prevailing climatic conditions.

*Flower type*.—The variety is considered to have a showy type flower.

*Flower size*.—Considered medium to large. Flower diameter at full bloom is approximately 32.0 millimeters.

*Bloom quantity*.—Considered abundant, approximately 50 flowers per meter, with a good distribution and a high rate of fruit set.

*Flower bud frequency*.—Generally 2 flower buds appear per node, occasionally 1.

*Petal size*.—Generally. — Considered medium.

*Length*.—Generally 18.0 to 19.0 millimeters.

*Width*.—Generally between 18.0 and 19.0 millimeters.

*Petal form*.—Round-shaped.

*Petal count*.—Generally 5.

*Petal texture*.—Smooth.

*Petal color*.—Both surfaces of the petal are colored with a pale Pink (RHS Red Purple 69 B to C) when young, becoming slightly darker until the end of blooming.

*Fragrance*.—Pronounced.

*Petal claw*.—Form. — The claw is considered to have a conic form, with a slightly round tip. Length. — Approximately 5.0 to 6.0 millimeters. Width. — Approximately 5.0 millimeters. Color. — A darker pink than the petal color.

*Petal margins*.—Generally considered slightly wavy.

*Petal apex*.—Generally. — The petal apices are generally wide dome-shaped.

*Flower pedicel*.—Length. — Considered medium to large and having an average length of approximately 4.0 to 5.0 millimeters. Diameter. — Considered average, approximately 2.0 millimeters. Color. — Brown (RHS Brown N 199 B to C).

*Calyx*.—Internal surface texture. — Smooth and glabrous. Color. — The inner surface of the calyx and the outer surface of the calyx are considered of purple-brown (RHS Greyed Purple 183 A to B, or RHS Grey Brown 199A) color.

*Sepals*.—Number. — Generally five sepals Surface texture. — The outer surface has a short, fine pubescent texture. Size. — Average. Length. — Approximately 5.0 to 6.0 millimeters. Width. — Approximately 4.0 to 5.0 millimeters. Form. — Ovoid shape Color. — Both sides of sepals are colored with a purple brown color (RHS Greyed Purple 183 A to B, or RHS Grey Brown 199A).

*Average number of stamens per flower*.—Approximately 43 stamens per flower.

*Anthers*.—Generally. — Medium in length. Color. — Orange yellow color (RHS Yellow Orange 16A) or red orange color (RHS Greyed Purple Group 178A). The anthers color may evolve with maturity to turn in a yellow color.

*Pollen production*.—Pollen is abundant, and has a yellow color (Approximately RHS Yellow Orange 17 B to C) which may evolve with maturity. The present variety is considered auto-fertile (self-pollinating).

*Filaments*.—Size. — Medium length, between 9.0 and 19.0 millimeters in length. Filaments length is generally equal or higher than the pistil's length. The stamen length is usually smaller than petals length.

*Color*.—Considered light pink to dark pink (approximately RHS Red Purple 62 C to D or RHS Red Purple 73 A to B). The color becomes darker during the blooming.

*Pistil*.—Number. — Usually 1. Generally. — Average in size. Length. — Approximately between 15.0 and 19.0 millimeters including the ovary. Generally equal to stamen length, if not slightly smaller. Color. — Considered a very pale green (RHS Yellow Green 150 D or RHS Yellow Green 151 D). The color evolves during the blooming. Surface texture. — The pubescence is present at the level of the ovary.

Fruit:

*Maturity when described*.—Very firm in ripe conditions (shipping ripe).

*Date of first picking*.—Jul. 21, 2008.

*Date of last picking*.—The date of harvest varies slightly with the prevailing climatic conditions. The 'CRISP-SUN' variety has a medium date of picking, and a grouped maturity. Usually, the maturity is grouped within approximately 10 days and the harvest is generally performed in two runs. Last known picking times carry on Jul. 21 to Aug. 2, 2008, then Jul. 30 to Aug. 5, 2009, then Aug. 5 to Aug. 23, 2010, then Jul. 16 to Jul. 25, 2011 and then Aug. 3 to Aug. 15, 2012.

*Size*.—Generally. — Fruits show a very round and regular shape and are not much hairy. Fruits are homogeneous in size, which is considered large.

*Average cheek diameter*.—Approximately 75.0 to 80.0 millimeters.

*Average axial diameter*.—Approximately 65.0 to 75.0 millimeters.

*Typical weight*.—Generally about 200.0 to 250.0 grams. This characteristic is high dependent upon the prevailing cultural practices, and therefore is not particularly distinctive of the variety.

*Fruit form*.—Generally. — Round. The fruit is generally uniform in symmetry, viewed from the suture's plane.

*Fruit suture*.—Wide-mouthed and slightly marked, extending from the base to the apex. No apparent callousing or stitching exists along the suture line. Not pointed.

*Suture*.—Color. — The suture has generally a similar color as the whole fruit color, a luminous red (RHS Orange Red 34 A).

*Ventral surface*.—Form. — Smooth and rounded.

*Apex*.—Non-prominent, generally slightly depressed.

*Base*.—Semi-flared, shallow.

*Stem cavity*.—Average depth of the stem cavity is about 12.0 to 14.0 millimeters. Average width is about 20.0 to 25.0 millimeters.

*Fruit skin*.—Thickness. — Considered thick and strong, and the adherence of skin to flesh is strong to medium, depending on the fruit maturity. Texture. — Short pubescence. Taste. — Semi-sweet, with a high level of sugars. Tendency to crack. — None observed.

*Color*.—Blush color. — This blush color is a luminous red (RHS Orange Red 34 A). The red blush covers 80% to 90% of the fruit skin surface on an orange background (RHS Orange Red 34 C or RHS Yellow Orange 14 A to B). The percentage of the blush on the fruit skin surface can vary, and is generally dependant upon the prevailing conditions under which the fruit was grown. Ground color. — The ground color covers approximately 10% to 20% of the fruit skin surface, and is considered orange (RHS Orange Red 34 C or RHS Yellow Orange 14 A to B).

*Fruit stem*.—Medium in length, approximately 7.0 millimeters.

*Diameter*.—Approximately 4.0 millimeters.

*Color*.—Pale green (RHS Yellow Green 145A to 145 B).

*Flesh*.—Ripens. — Very homogenously, slowly. The flesh has a long shelf life. Texture. — Very firm, very dense, crunchy, melting, juicy at harvest maturity stage. Fibers. — Generally not fibrous. Aroma. — Pronounced. Eating quality. — Considered very good, aromatic and sugary. Flavor. — Considered semi-sweet and very aromatic. The Brix is generally superior to 12 and acidity comprised between 6 and 9 meq/100 ml. Juice. — Very juicy at complete maturity. Brix. — Comprised between 12.0 and 15.0 degrees and generally superior to 12.0 degrees. This characteristic varies slightly with the number of fruit per tree; prevailing cultural practices; and the surrounding climatic conditions. Flesh color. — Orange yellow flesh (RHS Yellow Orange 14 B to C) with a slightly red pigmentation under the skin. The pit cavity is entirely pigmented with red color and around said cavity is a star-shaped red pigmentation.

Stone:

*Type*.—Clingstone, more or less adherent depending on the fruit maturity.

*Size*.—Considered medium for the variety. The stone size varies significantly depending upon the tree vigor, crop load and prevailing growing conditions.

*Length*.—Approximately 27.0 millimeters.

*Width*.—Approximately 20.0 millimeters.

*Diameter*.—Approximately 15.0 millimeters.

*Form*.—Elliptic.

*Base*.—Straight to slightly oblique.

*Apex*.—Shape. — The stone apex is prominent and pointed.

*Stone cavity*.—Considered medium size, with an ovate-form and dimensions corresponding to the stone's dimensions.

*Stone surface*.—Surface texture. — The pit is transversely furrowed on its entire surface. Furrows are more pronounced toward the apex. The stone is pitted toward the base. Relief is prominent generally and present basally. Ridges. — The surface texture is generally characterized by more prominent ridges along the ventral edges and is more prominent at the apical tip.

*Ventral edge*.—Width. — Considered small to medium, and having a dimension of approximately 2.0 millimeters at mid-suture.

*Dorsal edge*.—Shape. — Grooved.

*Stone color*.—The color of the dry stone is generally considered light orange brown (RHS Greyed Orange 173 C to D).

*Tendency to split*.—Splitting is usually absent, depending on climatic conditions between blooming period and stone hardening.

*Kernel*.—Size. — The kernel is considered medium. Length. — Approximately 20.0 millimeters. Width. — Approximately 12.0 millimeters. Thickness. — Approximately 3.0 to 4.0 millimeters. Form. — Considered oblate and elliptic. Pellicle. — Pubescent. Color. — The kernel skin is light orange-brown (RHS Greyed Orange 166 C) with slightly darker grooves (RHS Greyed Orange 166 B). The almond, which is the seed of the kernel, is cream white (RHS Orange White 159 D) and has a bitter tasting. The kernel and its embryo are mature at the time of fruit maturity.

*Use*.—The subject variety 'CRISPSUN' is considered to be a yellow peach tree of the medium season of maturity, and which produces fruits that are considered firm, attractively colored with a very luminous red. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long distance shipping.

*Keeping quality*.—Remarkable. Fruit have a slow maturation and a long shelf life both on the tree after growth completion and after harvesting without alteration. After growth completion, fruits are preserved on the tree more than 1 week. After harvest, fruits are well preserved more than 4 weeks at 2.0 degree Celsius.

*Shipping quality*.—Considered very good. The fruit of the new yellow peach variety showed minimal bruising of the flesh or skin damage after being subjected to normal harvesting and packing procedures. Its resistance to handling during harvest and packing and its long shelf life without alteration after harvest easily permit 3 to 4 weeks-shipping at 2 degrees Celsius.

*Resistance to disease*.—No particular susceptibilities were noted. The present variety is not very sensitive to powdery mildew and Monilia, or conservation diseases and decay due to its thick and strong skin. Although the new variety of peach tree possesses the described characteristics when grown under the ecological conditions prevailing near Elne, Pyrénées-Orientales department, France, it should be understood that variations of the usual magnitude and characteristics incident to changes in growing conditions, fertilization, pruning, pest control and horticultural management are to be expected.

We claim:

1. A new and distinct variety of yellow peach tree as illustrated and described, characterized by fruits with high eating quality and very long shelf life without alteration before and after harvesting, with a semi-sweet orange yellow flesh showing a red pigmentation under the skin, inside and around the pit cavity, and an attractive luminous skin with a high percentage of red blush on skin surface.

* * * * *